United States Patent [19]

Wijdenes et al.

[11] Patent Number: 5,717,073
[45] Date of Patent: Feb. 10, 1998

[54] ANTI-GP130 MONOCLONAL ANTIBODIES

[75] Inventors: John Wijdenes, Larnod; Claude Clement, Gray, both of France

[73] Assignee: Diaclone S.A. a Directoire et Conseil de Surveillance, Besancon, France

[21] Appl. No.: 634,736

[22] Filed: Apr. 18, 1996

[30] Foreign Application Priority Data

Apr. 21, 1995 [FR] France ................... 95 04809

[51] Int. Cl.$^6$ ................. C12N 5/12; C07K 16/00; A61K 39/395
[52] U.S. Cl. .................. 530/388.22; 435/327; 435/334; 530/388.85; 530/387.1; 424/141.1; 424/172.2; 424/152.2; 424/143.1
[58] Field of Search .................. 424/141.1, 143.1, 424/172.2, 152.2; 530/387.1, 388.22, 388.85; 435/334, 327

[56] References Cited

FOREIGN PATENT DOCUMENTS 0 572 118  12/1993  European Pat. Off. .

OTHER PUBLICATIONS

Wijdenes et al (Eur. J. Immunol., 1995, 25:3474–3481) Dec. 1995.
Johnston & Thorpe, Immunochemistry in Practice, Blackwell Scientific Pubs, Oxford, 1987, pp. 49–50.
The Journal of Biological Chemistry, vol. 267, No. 24, Aug. 25, 1992 Baltimore, MD pp. 16763–16766, J. Liu et al. "Interleukin–6 Signal Transducer GP130 Mediates Oncostatin M Signaling."

Journal of Immunological Methods, vol. 163, No. 2, Aug. 9, 1993 Amsterdam pp. 217–223, T. Saito et al. "Preparation Of Monoclonal antibodies against the IL–6 Signal Transducer, GP130, That Can Inhibit IL–6–Mediated Functions."

Biochemical and Biophysical Research Communications, vol. 185, No. 3, Jun. 30, 1992 Duluth, MN pp. 902–908, L. Snyers et al. "Enhancement Of IL–6 Receptor Beta Chain (GP130) Expression By IL–6, IL–1 And TNF In Human Epithelial Cells."

Proceedings of the National Academy of Sciences of the USA, vol. 89, No. 22, Nov. 15, 1992 Washington, DC pp. 10998–11001, T. Taga et al. "Functional Inhibition Of Hematopoietic and Neurotrophic Cytokines By Blocking The Interleukin 6 Signal Transducer GP130."

The 9th International Congress of Immunology; Meeting Sponsored By The American Association Of Immunologists And The International Union Of Immunological Societies, San Francisco, CA Jul. 23–29.

Annals of the New York Academy of Sciences, vol. 762, Jul. 21, 1995 New York, NY pp. 482–484, S. Chevalier et al. "Monoclonal Antibodies Define Different Functional Epitopes On GP130 Signal Transducer."

*Primary Examiner*—Paula K. Hutzell
*Assistant Examiner*—Susan Ungar
*Attorney, Agent, or Firm*—Oblon, Spivak, McClelland, Maier & Neustadt, P.C.

[57] ABSTRACT

The invention relates to anti-gp130 monoclonal antibodies, as well as to their uses for obtaining medicinal products, cell culture adjuvants and diagnostic reagents.

2 Claims, No Drawings

ANTI-GP130 MONOCLONAL ANTIBODIES

The invention relates to new monoclonal antibodies which recognize the glycoprotein gp130, and which can induce the proliferation of cell lines possessing this antigen, as well as to the use of said monoclonal antibodies for diagnosis and for obtaining medicinal products.

gp130 is a ubiquitous transmembrane glycoprotein which constitutes a signal transducer common to different cytokines belonging to the IL-6 (interleukin-6) family. Besides IL-6, cytokines concerned are CNTF (ciliary neurotropic factor), IL-11 (interleukin-11), LIF (leukemia inhibitory factor), OM (oncostatin M) [HIRANO et al. Stem Cells, 12, 262–277, (1994); ZHANG et al., J. Exp. Med., 177, 1337–1342 (1994)], cardiotrophin I [PENNICA et al., Proc. Natl. Acad. Sci. USA, 92, 1142–1146, (1995)], and the like.

Some of these cytokines (IL-11, LIF, OM) bind directly to gp130.

Others, and especially IL-6, combine beforehand with a specific receptor present on the cell membranes. This specific receptor, designated gp80 or IL-6R, has been described by TAGA et al. [J. Exp. Med., 166, 967–981, (1987)].

Transmission of the signal involves, first, the formation of an IL-6/IL-6R complex which then combines with gp130, and this induces homodimerization and then phosphorylation of the latter [MURAKAMI et al., Science, 260, 1808–1810, (1993)].

IL-6 and the cytokines of the same family are known to have a broad spectrum of biological functions; they participate, in particular, in the immune response, hematopoiesis, the nervous system, and the like. Consequently, a large number of studies have been directed towards obtaining molecules capable of modulating the activity of these cytokines.

Such molecules have, in effect, an important part to play in the study of the mechanisms governing the transmission of inter- and intracellular signals, and in the treatment of many diseases in which said cytokines participate.

Thus, the Inventors' team has previously obtained (French Patent 2,694,767 in the name of INNOTHERAPIE LABORATOIRES (S.A.)) monoclonal antibodies which recognize the IL-6R receptor, and are capable of inhibiting the interaction of IL-6 with IL-6R and the proliferation of IL-6-dependent cell lines.

TAGA et al. [Proc. Natl. Acad. Sci. USA, 89, 10998–11001 (1992)] describe anti-gp130 monoclonal antibodies which block the binding of the IL-6/IL-6R complex to gp130, and the cell proliferation (evaluated by DNA neosynthesis) induced by the activation of gp130 resulting therefrom.

The Inventors have now isolated new hybridoma cell lines producing anti-gp130 monoclonal antibodies, and have found that, most surprisingly, some of these antibodies were capable of mimicking the effector action of the different cytokines whose signals are transmitted by gp130.

The subject of the present invention is monoclonal antibodies directed against the gp130 receptor, which antibodies are chosen from the group consisting of:
- the IgG1 isotype monoclonal antibody designated B-S12, produced by the hybridoma line deposited on Apr. 12, 1995 with the C.N.C.M. (NATIONAL COLLECTION OF MICROORGANISM CULTURES held by the PASTEUR INSTITUTE, 28, rue du Docteur Roux, 75724 PARIS CEDEX 15 (FRANCE)) under the Deposit Number I-1561;
- the IgG1 isotype monoclonal antibody designated B-P8, produced by the hybridoma line deposited on Apr. 12, 1995 with the C.N.C.M. under the Deposit Number I-1560.

The invention also encompasses class switching variants of the above antibodies, such as, for example, variants belonging to the isotypes IgG3, IgG1, IgG2b, IgG2a and other immunoglobulin subclasses; such variants may be obtained, for example, by the method described by COCO MARTIN et al. [J. Immunol. Methods, 145, p. 1118, (1991)].

The Inventors also found that the monoclonal antibodies according to the invention induce, like the IL-6/IL-6R complex, the phosphorylation of gp130; now, this phosphorylation is known to necessitate the prior dimerization of gp130 [MURAKAMI et al., Science, (1993), publication cited above]. It is probable that the monoclonal antibodies according to the invention act according to a mechanism similar to that of the IL-6/IL-6R complex, by inducing the homodimerization and then the phosphorylation of gp130.

This supposed mechanism of action would explain the observation made by the Inventors, according to which Fab fragments of B-S12 recognize gp130 but do not have a biological effect.

The monoclonal antibodies B-S12 and B-P8 recognize different epitopes: the epitope recognized by B-S12 is located in the region designated WSXWS box [BAZAN, Proc. Natl. Acad. Sci. USA, 87, 6934–6938 (1989); GEARING et al., EMBO J., 8, 3667–3676 (1989)].

As a result of their mechanism of action, similar to that of the IL-6/IL-6R complex, the monoclonal antibodies according to the invention may be used, like the IL-6/IL-6R complex [YOSHIDA et al., Mechanisms of Development, 45, 163–171 (1994)], for the setting up and maintenance in culture of stem cells carrying gp130, such as, for example, hematopoietic stem cells [BERARDI et al., Science, 267, 104–107, (1995)], pluripotent embryonic stem cells [NICHOLS et al., Experimental Cell Research, 215, 237–239 (1994)], and the like.

For this use, the monoclonal antibodies according to the invention may be employed at concentrations between 1 and 25 µg/ml, and preferably 10 µg/ml; they are added to the culture medium at the beginning of culture.

The monoclonal antibodies according to the invention may also be used in pathologies for which the cytokines whose signals are transmitted via gp130 have a beneficial effect and may bring about an improvement.

Monoclonal antibodies according to the invention may be used alone or alternatively coupled to toxins, or to radioactive substances or to any other therapeutic agent. They may also be encapsulated in liposomes.

Pharmaceutical preparations comprising monoclonal antibodies according to the invention may be presented in liquid form or in lyophilized form. In order to stabilize these pharmaceutical preparations, proteins, sugars, sugar alcohols or amino acids may be used; to buffer them, inorganic salts, preferably sodium phosphate in a physiological saline, (PBS, pH 7.4) may be used; it is also possible to use various agents to increase their viscosity.

The antibodies according to the invention are used at concentrations of between 0.5 and 5 mg/ml, and preferably 1 mg/ml, when they are used for therapeutic purposes. Generally speaking, the therapeutic preparations containing the antibodies according to the invention are administered systemically, though local administration is not ruled out.

Monoclonal antibodies according to the invention may be used not only in therapy, but also for prophylactic purposes.

The antibodies according to the invention may be used separately; preferably, they will be used together. In effect, the Inventors found a synergy of action between B-S12 and B-P8 antibodies.

The monoclonal antibodies according to the invention may also be used as diagnostic reagents for identifying the gp130 antigen, or an epitope of the latter, on the surface of cells or in biological fluids. For such uses, the monoclonal antibodies may be coupled to fluorescent, biotinylated, radioactive or other labels. It is also possible to use the monoclonal antibodies according to the invention in ELISA or RIA tests in order to assay gp130 in biological fluids. The monoclonal antibodies according to the invention may also be used to identify and purify gp130, or epitopes of said receptor, from preparations of macromolecules likely to contain said receptor or its epitopes, such as, for example, cell lysates and fractions, or peptide or oligosaccharide preparations resulting, for example, from the enzymatic digestion of a cell fraction or alternatively obtained by chemical synthesis.

The monoclonal antibodies according to the invention also make it possible to obtain chimeric antibodies whose constant domain is of human origin (human immunoglobulin) and whose variable portion, or preferably hypervariable portion, is of murine origin (murine immunoglobulin). For the treatment of diseases in which gp130 is involved, these chimeric antibodies may be used either pure or else coupled to toxins, radioactive substances or other medicinal substances, or alternatively encapsulated in liposomes.

A better understanding of the present invention will be gained from the additional description which follows, which refers to examples of preparation and use of the monoclonal antibodies according to the invention.

It is, however, self-evident that these examples are given only by way of illustration of the subject-matter of the invention, and cannot be considered in any way to constitute a limitation thereof.

I. PREPARATION OF MONOCLONAL ANTIBODIES

Example 1

Immunization, fusion, cloning and harvesting of monoclonal antibodies

An immunization protocol derived from that described by MATTHEW and SANDROCK [J. Immunol. Methods, 100, 73–82, (1987)] was used.

Female Balb/C mice underwent an intraperitoneal injection of 2 µg of soluble gp130. This protocol was repeated three times at two-week intervals, after which the fourth injection was carried out intravenously and the spleen cells were extracted four days later and fused. Fusion was performed in the following manner: spleen cells were fused with mouse myeloma cells designated X63Ag8653 (spleen cell/myeloma cell ratio is 5:1) in the presence of polyethylene glycol [KEARNEY et al., J. of Immunol., 123, 1548, (1978)]. The cell line X63Ag8653 is deposited with the EUROPEAN COLLECTION OF ANIMAL CELL CULTURES (ECACC), PHLS Center of Applied Microbiology and Research, Porton Down, Salisbury, Wiltshire, SP4 0JG, UK, under the Deposit Number ECACC 850 114 20.

The suspension of fused cells was washed once and cultured on selective medium (RPMI 1640, 10% heat-inactivated horse serum, 4 mM glutamine, 13.6 mg/l of hypoxanthine, 0.17 mg/l of aminopterin and 10 µg/ml of insulin).

Ten days after fusion, the supernatants of the cultures in which hybridoma growth was observed were tested to detect the production of anti-IL-6R monoclonal antibodies.

For this purpose, 75 µl of supernatant of each hybridoma culture were tested by flow cytometry on BAF (gp130-negative) and BF130/80 (gp130-positive) cell lines.

Hybridomas producing antibodies which recognize the BAF130/80 line were selected and were cloned four times using the limiting dilution method (inoculation density 0.2 cell per culture well).

Example 2

Production in vivo and purification of monoclonal antibodies

Monoclonal antibodies are produced in large amounts in vivo by intraperitoneal injection of B-S12 and B-P8 hybridoma cells in Balb/c mice. One week after the injection of hybridoma cells, the mice receive an intraperitoneal injection of 0.5 ml of Freund's incomplete adjuvant. The ascites fluid is recovered 8 to 14 days after injection of the cells.

The monoclonal antibodies are then precipitated from the ascites fluid by adding ammonium sulfate (45%), buffered to pH 7.7 with 0.02 mM Tris and bound to a column of Sepharose Q. The antibodies bound to the column are washed with 1% Tween 20 in 0.02 mM Tris, pH 7.7, and then eluted from the column with a 0.02 mM Tris, 0.035M NaCl, pH 7.7 solution.

II. BIOLOGICAL ACTIVITY OF B-S12 AND B-P8 ANTIBODIES

Example 3

Induction of the proliferation of the IL-6-dependent human cell line XG1 with the antibodies B-S12 and B-P8

The human cell line XG1 is a myeloma line whose proliferation and properties depend on IL-6, and which has been described by KLEIN [BLOOD, 74, 749, (1989)].

For the experiments, the XG1 line is cultured for three days in RPMI 1640 medium in the presence of 10% fetal calf serum and β-mercaptoethanol, as well as:

either 100 pg (=10 units) of IL-6 per culture well;

or various concentrations of the antibodies B-S12 or B-P8.

A control consists of cells cultured in the absence of IL-6 and of antibodies.

The cells are then cultured for 16 hours in the presence of [$^3$H]thymidine which is incorporated in the newly synthesized DNA, enabling cell growth to be evaluaed, and they are then collected and the radio-activity is measured in a beta counter.

Measurements are made in parallel on the cells cultured in the absence of IL-6 and in the presence of various concentrations of the antibodies B-S12 and/or B-P8, on the cells cultured without antibodies in the presence of IL-6 and on the control cells.

The mean radioactivity measured on the control cells is 8000 cpm.

The mean radioactivity measured in cells cultured in the presence of IL-6 without antibodies is 55,000 cpm.

The results obtained in the absence of IL-6 and in the presence of increasing concentrations of the antibodies B-S12 or B-P8 are shown in Table I below:

TABLE I

| CONCENTRATION (ng) | B-S12 | B-P8 | B-P8 + 16 ng B-S12 |
|---|---|---|---|
| | RADIOACTIVITY (CPM) | | |
| 2000 | 43720 | 40328 | 57342 |
| 400 | 44201 | 13031 | 57867 |
| 80 | 38782 | 8095 | 56816 |
| 16 | 32494 | 8203 | 52541 |
| 3.2 | 11383 | 8529 | 54785 |
| 0.64 | 9000 | 7690 | 45868 |
| 0.128 | 9600 | 7000 | 38921 |

These results show clearly that cell growth is similar in the case of cells cultured in the presence of the monoclonal antibodies B-S12 and B-P8 and in control cells cultured in the presence of IL-6 without antibodies. Hence these two antibodies stimulate, independently of the presence of IL-6, the growth of the XG1 cell line. In addition, a synergy of action between these two antibodies is clearly observed.

Example 4

Induction of the proliferation of the human cell line TF-1 with the antibody B-S12

The human cell line TF-1 is an erythroleukemic line which has been described by KITAMURA et al. [J. Cell. Physiol. 140, 323–334 (1989)].

For the experiments, the TF-1 line is cultured for three days in RPMI 1640 medium in the presence of 10% fetal calf serum, as well as:

either 2000 pg (=10 units) of IL-6 per culture well;

or various concentrations of the antibodies B-S12 or B-P8.

A control consists of cells cultured in the absence of IL-6 and of antibodies.

The cells are then cultured for 16 hours in the presence of [$^3$H]thymidine and they are then collected, and the radioactivity is measured in a beta counter.

Measurements are made in parallel:

on the cells cultured in the absence of IL-6 and in the presence of various concentrations of the antibodies B-S12 or B-P8, on the cells cultured without antibodies in the presence of IL-6, on the control cells.

The mean radioactivity measured on the control cells is 1500 cpm.

The mean radioactivity measured in cells cultured in the presence of IL-6 without antibodies is 18,000 cpm.

The results obtained in the presence of increasing concentrations of the antibodies are shown in Table II below:

TABLE II

| CONCENTRATION (µg) | B-S12 | B-P8 |
|---|---|---|
| | RADIOACTIVITY (CPM) | |
| 10 | 11265 | 13260 |
| 1 | 10855 | 3077 |
| 0.1 | 6775 | 1800 |

These results show that cells cultured in the presence of the monoclonal antibodies B-S12 and B-P8 display cell growth of an order of magnitude comparable to that of control cells cultured in the presence of IL-6 without antibodies.

Example 5

Effect of antibodies which block IL-6-induced proliferation on the proliferation induced by B-S12 and B-P8

The human cell line XG1 is cultured as described in Example 3 above, in the presence of:

either 40 pg (=4 units) of IL-6 per culture well;

or various concentrations of the antibodies B-S12 and B-P8, in the presence or absence of 10 µg of one or other of the blocking antibodies B-E8 (anti-IL-6, described in the European Patent Application filed under the number 90 122694.4) or B-R6 (anti-IL-6R, described in the French Patent Application published under the number 2,694,767).

A control consists of cells cultured in the absence of IL-6 and of antibodies.

The cells are then cultured and the radio-activity is measured as described in Example 3 above.

The mean radioactivity measured on the control cells is 9000 cpm.

The mean radioactivity measured in cells cultured in the presence of 4 units of IL-6 without antibodies is 60,000 cpm; the mean radioactivity measured in cells cultured in the presence of 4 units of IL-6 and 10 µg of the antibody B-E8 or B-R6 is 10,000 cpm.

The results obtained for various concentrations of B-S12 and B-P8 are shown, respectively, in Tables III and IV below:

TABLE III

| CONCENTRATION | B-S12 | B-S12 + B-E8 | B-S12 + B-R6 |
|---|---|---|---|
| | RADIOACTIVITY (CPM) | | |
| 0 | — | 9340 | 9328 |
| 10 µg | 67527 | 63589 | 63240 |
| 1 µg | 58930 | 58773 | 58879 |
| 100 ng | 49441 | 53158 | 50911 |
| 10 ng | 40888 | 32280 | 31492 |
| 1 ng | 14518 | 16654 | 20575 |
| 100 pg | 10057 | 10516 | 12530 |

TABLE IV

| CONCENTRATION | B-P8 | B-P8 + B-E8 | B-P8 B-R6 |
|---|---|---|---|
| | RADIOACTIVITY (CPM) | | |
| 0 | — | 10213 | 10200 |
| 10 µg | 51363 | 49115 | 56268 |
| 1 µg | 16405 | 13107 | 15702 |
| 100 ng | 9526 | 10567 | 12094 |
| 10 ng | 10309 | 9298 | 12322 |

These results show that the proliferation of the XG1 cell line induced by B-S12 and B-P8 is not blocked by the antibodies B-E8 and B-R6, contrary to IL-6-induced proliferation.

Example 6

Induction of haptoglobin secretion by the human cell line HepG2 with the antibody B-S12

For the experiments, the hepatoma line HepG2 (ECACC No. 8501/1430; ATCC Designation: HB8065) is cultured in ISCOVE medium for two days in the presence of 10% fetal calf serum and dexamethasone ($10^{-6}$M), as well as:

either various concentrations of oncostatin M (OM) per culture well;

or various concentrations of the antibody B-S12 or of a control, "irrelevant" monoclonal antibody (that is to say one recognizing an antigen unrelated to gp130).

A control consists of cells cultured in the absence of OM and of antibodies.

After 48 hours of culture, the supernatants are harvested and their concentration is determined by ELISA.

The results obtained in the presence of increasing concentrations of OM (expressed in ng/ml) and of the antibodies (expressed in µg/ml) are shown (in ng of haptoglobin per ml) in Table V below:

TABLE V

| Concentration of OM (ng/ml) or of antibodies (µg/ml) | OM | B-S12 | IRRELEVANT MAb |
|---|---|---|---|
| | Haptoglobin secretion (ng/ml) | | |
| 0 | 7.5 | 4 | 2 |
| $10^{-5}$ | 9 | 5 | 2.5 |
| $10^{-4}$ | 10 | 7 | 2 |
| $10^{-3}$ | 12.5 | 9 | 3 |
| $10^{-2}$ | 15 | 12 | 4 |
| $10^{-1}$ | 27 | 20 | 3 |
| 1 | 50 | 27 | 3.5 |
| 10 | — | 40 | 4 |

These results show a significant induction of haptoglobin secretion in cells cultured in the presence of the monoclonal antibody B-S12.

Example 7

Properties of the Fab fragments of B-S12

Fab fragments of B-S12 are obtained by papain cleavage.

1) RECOGNITION OF gp130 BY THE Fab FRAGMENTS

BAF130/80 (gp130-positive) cells are incubated for 30 minutes in the presence of variable concentrations of B-S12 Fab or of B-S12. After incubation, the cells are washed twice and incubated with fluorescein-labeled goat anti-mouse serum for 30 minutes, washed again and analyzed by flow cytometry.

Table VI below shows the percentage of cells labeled by each of the different reagents (Fab or whole antibody) used at decreasing concentrations.

TABLE VI

| CONCENTRATION (µg/ml) | B-S12 | B-S12 Fab |
|---|---|---|
| 10 | 36 | 42 |
| 5 | 69 | 48 |
| 2.5 | 70 | 52 |
| 1.25 | 73 | 55 |
| 0.625 | 73 | 53 |
| 0.312 | 71 | 50 |
| 0.156 | 67 | 42 |
| 0.08 | 60 | 30 |
| 0.04 | 49 | — |
| 0.02 | 36 | 9 |
| 0.01 | 23 | — |
| 0.005 | 18 | — |

2) BIOLOGICAL ACTIVITY OF THE Fab FRAGMENTS

The biological activity is determined on XG1 cells according to the protocol described in Example 3.

Measurements are made in parallel on the cells cultured in the absence of IL-6 and in the presence of various concentrations of the Fab fragments and of the whole B-S12 antibody, on the cells cultured without antibody in the presence of IL-6 and on the control cells.

The mean radioactivity measured on the control cells is 4000 cpm.

The mean radioactivity measured in cells cultured in the presence of IL-6 without antibodies is 44000 cpm.

The results obtained in the presence of decreasing concentrations of the Fab fragments and of the whole B-S12 antibody are shown in Table VII below:

TABLE VII

| CONCENTRATION (ng) | B-S12 | B-S12 Fab |
|---|---|---|
| | RADIOACTIVITY (CPM) | |
| 10000 | 30466 | 2826 |
| 2000 | 29157 | 3100 |
| 400 | 31008 | 4200 |
| 80 | 27372 | 4990 |
| 16 | 22038 | 4040 |
| 3.2 | 9240 | 4360 |
| 0.64 | 4296 | 4200 |

These results show that the Fab fragments, while they recognize the gp130 antigen, are incapable of inducing the growth of the XG1 cell line.

Example 8

Analysis of the phosphorylations induced by the antibody B-S12

The human neuroblastoma line SK-N-MC [BIEDLER J. L., HELRON and SPENGLER, B. A., CANCER RESEARCH, 33, p. 2643, (1973)] strongly expresses the gp130 transduction subunit of the IL-6, IL-11, LIF, CNTF, OM and cardiotrophin-1 receptors.

During the binding of the ligands to their receptors, the gp130 chain is very rapidly phosphorylated by submembrane kinases of the JAK family [STAHL et al., Science, 263, p. 92, (1994)] in order to be able to accept the binding of proteins of the STAT family [IHLE and KERR, TIG, 11:2 69–74, (1995)]. The latter proteins, after contact with gp130, are then translocated to the nucleus in order to deliver afferent information thereto [STAHL et al., Science, 267, p. 1349, (1995)].

SK-N-MC cells in an exponential phase of culture are deprived of serum for 5 h in order to slow down the endogenous phenomena of constitutive phosphorylation.

A cytokine (OM, 50 ng/ml) or the antibody B-S12 are added to the cultures, respectively, for:

10 minutes and 20 minutes for a first experiment, or 5 to 30 minutes for a second experiment.

The culture medium (RPMI 1640) is then removed and replaced by 1 ml of lysis buffer (10 mM Tris, pH 7.6, 5 mM EDTA, 30 mM sodium pyrophosphate, 1 mM sodium fluoride, 1 mM orthovanadate, 1% TRITON X-100). The samples are then stirred for 1 h before being centrifuged (30 minutes, 12000 rpm, 4° C).

The pellet is removed, and gp130 or the JAK kinases are immunoprecipitated using, respectively, anti-gp130 antibody (10 µg/well) or anti-JAK1 and anti-JAK2 polyclonal antibodies (UBI; distributed by EUROMEDEX, BP80, 67460 SOUFFELWEYERSHEIM, FRANCE) diluted to 1/100. The Ab-Ag complex is isolated by adding 20 µl of a solution of protein A-coated beads. After 2 h of contact, the beads are washed 4 times by centrifugation with the lysis buffer before being taken up in the LAEMLI sample buffer containing 2-ME as reducing agent. The sample is heated to boiling for 10 minutes in order to liberate again the constituents of the immunoprecipitated complex, before being loaded onto a conventional 7.5% SDS-PAGE electrophoresis gel. After migration for 2 h, the samples are transferred onto an IMMOBILON (AMERSHAM) membrane by electro-transfer.

After saturation of the nonspecific adsorption sites by incubation overnight in the presence of a 200 mM NaCl, 50 mM Tris, pH 7.6, 6% BSA solution, the membrane is incubated for 4 h in the presence of an antibody which recognizes the phosphotyrosine motif 4G10 (UBI) at a concentration of 0.5 µg/ml. After 4 washes in 200 mM NaCl, 50 mM Tris, pH 7.6, 0.05% Tween 20 buffer, an anti-rabbit immunoglobulin antibody coupled to peroxidase (TAGO; distributed by BIOSOFT, 60 rue de Wattignies, 75580 PARIS CEDEX 12, FRANCE) is added at a dilution of 1/2000.

After 1 h of contact, the membrane is washed 5 times and its contents are revealed with the ECL kit from AMERSHAM (RPN 2106). The photon emission generated is visualized using an AMERSHAM RPN 2103 film.

A phosphorylation signal is detectable at and above an antibody concentration of 5 µg/ml; this signal increases in intensity up to 50 µg/ml (the highest concentration tested).

An analysis of the kinetics of the phenomenon shows that the latter reaches a maximal intensity after 20 minutes of contact before decreasing after 30 minutes. A control IgG1 isotype antibody incubated with the cells for 20 minutes is without any effect on the activation of gp130. Hence the observed phenomenon is indeed dependent on the variable portion of the antibody B-S12.

These experiments show that the antibody B-S12 is capable of inducing, in a dose-dependent manner, a phosphorylation of the gp130 signal transduction protein.

Other results show that the antibody B-S12 is actually capable of stimulating the autophosphorylation of the 2 submembrane kinases, JAK1 and 2, involved in the phenomena of phosphorylation of gp130, in a manner similar to that which has been reported for the ligands [STAHL et al., Science, 263, p. 92, (1994)].

Example 9

Measurement of soluble gp130 by sandwich ELISA

The working protocol is as follows:
- Incubation of microtitration plates with the antibodies B-S12 or B-P4 (anti-gp130 MAb which recognize an epitope other than that recognized by B-S12) (0.5 µg/well in 100 µl of PBS buffer) overnight at 4° C.
- Saturation with PBS buffer containing 5% of albumin for 90 minutes at room temperature.
- Distribution in each well of the plate of 100 µl of human serum at variable dilutions (human serum contains soluble gp130) and 50 µl of biotinylated antibody B-S12 or B-P4, and incubation for 2 h at room temperature.
- Distribution in the wells of a solution of peroxidase-labeled streptavidin and then of its substrate TMB (TMB=3,3',5,5'-tetramethylbenzidine), and measurement of the optical density at 450 nm after blocking the reaction with 100 µl of 1N $H_2SO_4$.

The results expressed in optical density (OD) are recorded in Table VIII below for each of the combinations of antibodies.

TABLE VIII

| SERUM (dilution) | BP4 + BP4$_{biot}$ | BS12 + BS12$_{biot}$ | BP4 + BS12$_{biot}$ | BS12 + BP4$_{biot}$ |
|---|---|---|---|---|
| Pure | 0.213 | 0.452 | >2.800 | >2.800 |
| 1/10 | 0.277 | 0.123 | 2.220 | 1.956 |
| 1/100 | 0.240 | 0.135 | 2.080 | 1.870 |
| 0 | 0.236 | 0.143 | 0.134 | 0.138 |

BS-12 enables the soluble gp130 of human serum, pure and diluted 1/10 and 1/100, to be measured, provided it is used in combination with an antibody which recognizes another epitope of gp130.

These results show that the epitope recognized by B-S12 is not repeated on soluble gp130. The very low signal observed in the case of the use of the combination of BP12 and BS12$_{biot}$ with pure human serum reflects the small proportion of dimer forms of gp130.

We claim:

1. A monoclonal antibody, with agonist activity, directed against the gp130 receptor, which is chosen from the group consisting of:

the IgG1 isotype monclonal antibody designated B-S12, produced by the hybridoma line deposited on Apr. 12, 1995 with the C.N.C.M. under the Deposit Number I-1561, the IgG1 isotype monoclonal antibody designated B-P8, produced by the hybridoma line deposited on Apr. 12, 1995 with the C.N.C.M. under the Deposit Number I-1560, and class switching variants of antibodies B-S12 and B-P8.

2. A composition which comprises as active principle at least one antibody according to claim 1 with a pharmaceutically acceptable carrier.

* * * * *